United States Patent

Kompis et al.

[11] 3,931,181
[45] Jan. 6, 1976

[54] 2,4-DIAMINO-5-BENZYLPYRIMIDINES

[75] Inventors: Ivan Kompis, Oberwil; Gerald Rey-Bellet, Basel; Guido Zanetti, Fullinsdorf, all of Switzerland

[73] Assignee: Hoffmann-La Roche Inc., Nutley, N.J.

[22] Filed: July 16, 1974

[21] Appl. No.: 489,050

[30] Foreign Application Priority Data
July 27, 1973 Switzerland.................. 10995/73

[52] U.S. Cl.................. 260/256.4 N; 260/256.4 C; 260/256.5 R; 424/251
[51] Int. Cl.²................................... C07D 239/00
[58] Field of Search............... 260/256.4 C, 256.4 N, 256.5 R

[56] References Cited
UNITED STATES PATENTS

| | | | |
|---|---|---|---|
| 3,341,541 | 9/1967 | Hoffer et al. | 260/256.4 N |
| 3,644,364 | 2/1972 | Anthony | 260/256.4 N |

*Primary Examiner*—Donald G. Daus
*Assistant Examiner*—James H. Turnipseed
*Attorney, Agent, or Firm*—Samuel L. Welt; Bernard S. Leon; William G. Isgro

[57] ABSTRACT

2,4-Diamino-5-benzylpyrimidines characterized by the formula

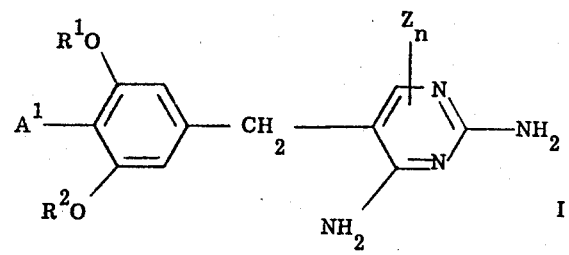

wherein $R^1$, $R^2$, $A^1$, $Z$ and $n$ are as hereinafter set forth, are described. The 2,4-diamino-5-benzylpyrimidines of the invention have useful antibacterial activity. More particularly, they block bacterial dihydrofolate reductase and potentiate the antibacterial activity of sulfonamides.

21 Claims, No Drawings

2,4-DIAMINO-5-BENZYLPYRIMIDINES

BRIEF SUMMARY OF THE INVENTION

The invention relates to compounds characterized by the formula

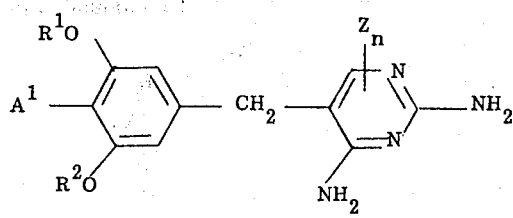

I wherein $R^1$ and $R^2$ are lower alkyl or lower alkenyl; Z is an oxygen atom bonded to one of the cyclic nitrogen atoms; $n$ is 0 or 1; and $A^1$ is trifluoromethyl,

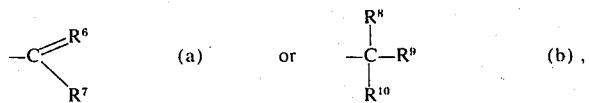

wherein $R^6$ is oxo and $R^7$ is hydrogen, lower alkyl or lower alkoxy, or $R^6$ is hydroxyimino and $R^7$ is lower alkyl, or $R^6$ together with $R^7$ is nitrilo; $R^8$ and $R^9$ are hydrogen or lower alkyl; $R^{10}$ is hydroxy, lower alkoxy or $-N(R^3,R^4)$ wherein $R^3$ and $R^4$, individually, are hydrogen, lower alkyl or lower alkanoyl, or $R^9$ and $R^{10}$, individually, are lower alkoxy or lower alkylthio, or $R^9$ taken together with $R^{10}$ are lower alkylenedioxy or lower alkylenedithio, and pharmaceutically acceptable acid addition salts thereof.

In another aspect, the invention relates to various processes for preparing the compounds of formula I.

DETAILED DESCRIPTION OF THE INVENTION

The invention relates to 2,4-diamino-5-benzyl-pyrimidines of the formula

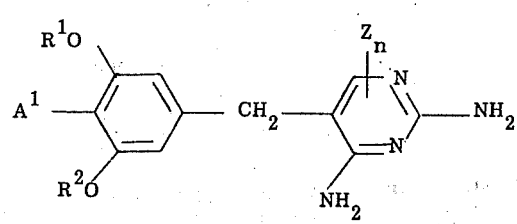

I wherein $R^1$ and $R^2$, individually, are lower alkyl or lower alkenyl; Z is an oxygen atom bonded to one of the cyclic nitrogen atoms; n is 0 or 1; and $A^1$ is trifluoromethyl,

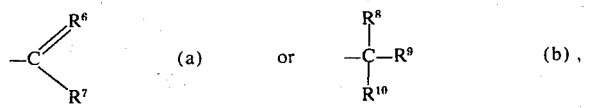

wherein $R^6$ is oxo and $R^7$ is hydrogen, lower alkyl or lower alkoxy; or $R^6$ is hydroxyimino and $R^7$ is lower alkyl, or $R^6$ together with $R^7$ is nitrilo; $R^8$ and $R^9$, individually, are hydrogen or lower alkyl; $R^{10}$ is hydroxy, lower alkoxy, or $-N(R^3,R^4)$, wherein $R^3$ and $R^4$, individually, are hydrogen, lower alkyl or lower alkanoyl, or $R^9$ and $R^{10}$, individually, are lower alkoxy or lower alkylthio, or $R^9$ taken together with $R^{10}$ is lower alkylenedioxy or lower alkylenedithio, and pharmaceutically acceptable acid addition salts of such compounds.

As used herein, the term "lower alkyl" denotes straight-chain or branched chain saturated aliphatic hydrocarbons of at the most 4 carbon atoms, that is, 1 to 4 carbon atoms, such as methyl, ethyl, propyl, and the like. The term "lower alkoxy" denotes a straight chain or branched chain saturated aliphatic ether wherein the alkyl moiety is as hereinbefore described, for example, methoxy, ethoxy, and the like. The term "lower alkylthio" denotes a straight chain or branched chain saturated aliphatic thioether wherein the alkyl moiety is as hereinbefore described, for example, methylthio, ethylthio, and the like. As used herein, the term "halogen" denotes chlorine, bromine, fluorine and iodine. The term "lower alkenyl" denotes straight chain or branched chain olefinically unsaturated hydrocarbon of up to 3 carbon atoms, that is, 2 to 3 carbon atoms, such as allyl and the like. The term "lower alkanoyl" denotes a straight chain or branched chain radical of an alkane carboxylic acid of 1 to 4 carbon atoms, for example, formyl, acetyl, and the like. The term "lower alkylenedioxy" or "lower alkylenedithio" denotes a dioxy or dithio residue of 2 to 3 carbon atoms.

The group

(a) comprises, for example, the radical cyano, lower alkoxycarbonyl, N-hydroxyimino-lower alkyl, formyl or lower alkylcarbonyl.

The group

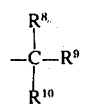

(b) comprises, for example, the radicals lower alkyl-di-lower alkoxymethyl, lower alkyl-lower alkylenedioxymethyl, lower alkyl-di-lower alkylthiomethyl, lower alkyl-lower alkylenedithiomethyl, optionally C-mono- or -di-lower alkylated hydroxymethyl, optionally C-mono- or -di-lower alkylated-lower alkoxymethyl, optionally C-mono- or -di-lower alkylated aminomethyl, optionally C-mono- or -di-lower-alkylated lower alkylaminomethyl, optionally C-mono- or -di-lower alkylated di-lower alkyl-aminomethyl.

A preferred subgenus of the invention comprises the compounds of the formula I wherein $R^1$ and $R^2$ are lower alkyl, especially methyl, ethyl. Further preferred are compounds of the formula I wherein $A^1$ is C-mono- or -di-lower alkylated hydroxymethyl, C-mono- or -di-lower alkylated lower alkoxymethyl, or lower alkylcarbonyl.

The benzylpyrimidines of the formula I and their salts can be prepared by the following processes:

a. reacting a compound of the formula

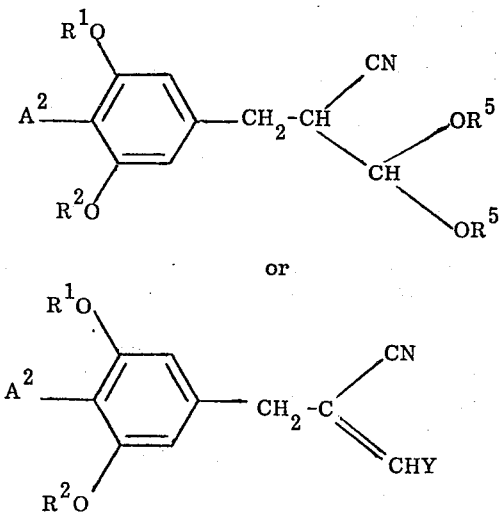

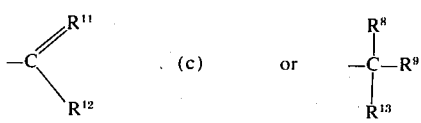

wherein $R^5$ is lower alkyl; Y is a leaving group and $A^2$ is trifluoromethyl,

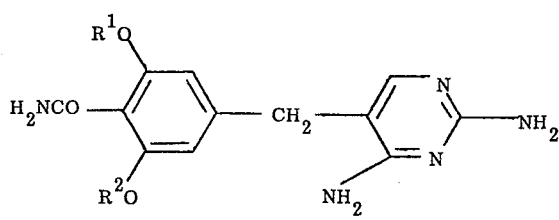

wherein $R^{11}$ is oxo and $R^{12}$ is lower alkoxy, or $R^{11}$ taken together with $R^{12}$ are nitrilo; $R^{13}$ is hydroxy, lower alkoxy or $-N(R^3,R^4)$; or $R^9$ taken together with $R^{13}$ are lower alkylenedioxy or lower alkylenedithio; and $R^1$, $R^2$, $R^3$, $R^4$, $R^8$ and $R^9$ are as hereinbefore with guanidine, or by b. dehydrating a compound of the formula

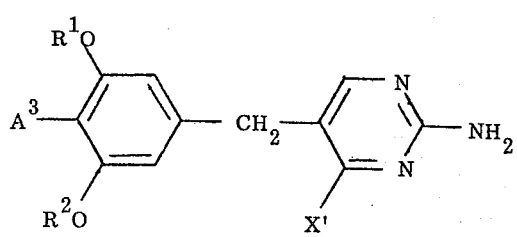

wherein $R^1$ and $R^2$ are as hereinbefore described, to the nitrile or by c. reacting a compound of the formula

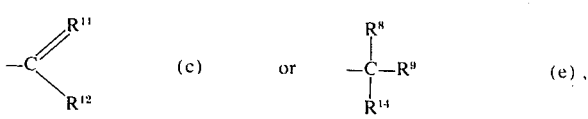

wherein X' is chloro, bromo, lower alkylthio or lower alkylsulfonyl, and $A^3$ is trifluoromethyl,

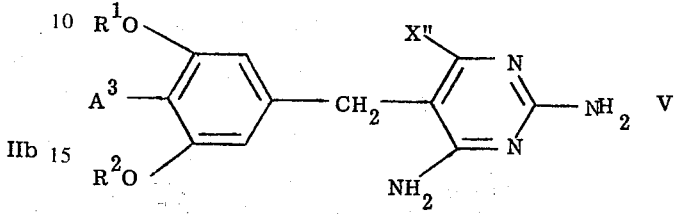

wherein $R^{11}$ is oxo and $R^{12}$ is lower alkoxy, or $R^{11}$ taken together with $R^{12}$ are nitrilo; $R^{14}$ is lower alkoxy, or $-N(R^3,R^4)$ or $R^9$ taken together with $R^{14}$ are lower alkylenedioxy; and $R^1$, $R^2$, $R^3$, $R^4$, $R^8$ and $R^9$ are as hereinbefore described with ammonia, or by d. replacing the substituent X'' in a compound of the formula

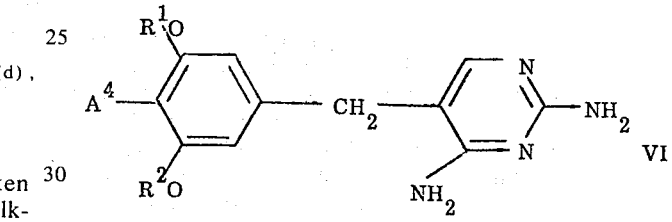

wherein $R^1$, $R^2$ and $A^3$ are as hereinbefore described, and X'' is chloro, bromo or hydroxy with a hydrogen atom, or by e. treating a compound of the formula

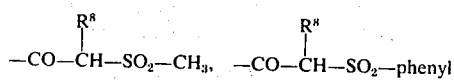

wherein $A^4$ is

and $R^1$, $R^2$ and $R^8$ are as hereinbefore described, with aluminum amalgam, whereby the group $A^4$ is reductively cleaved to the acetophenone group, or by f. subjecting a compound of formula I, wherein n is 0, to N-oxidation, or by g. hydrolytically or hydrogenolytically cleaving the amino protecting groups in a compound of the formula

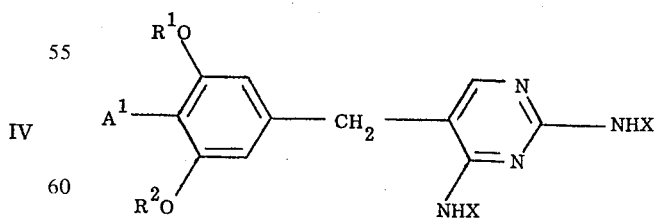

wherein X is hydrogen or an amino protecting group, provided that at least one X is an amino protecting group, and $R^1$, $R^2$ and $A^1$ are as hereinbefore described or by h. esterifying or reducing to the aldehyde the carboxyl group of a compound of the formula

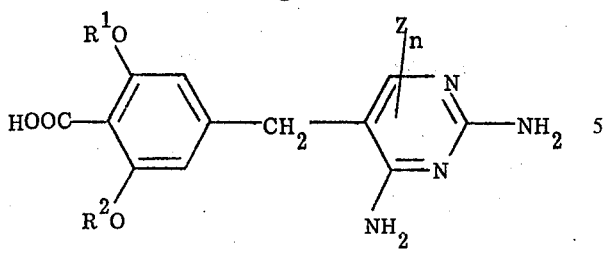

Ia wherein $R^1, R^2$, Z and n are as hereinbefore described,
or i. in a compound of formula I, wherein $A^1$ is lower alkylcarbonyl and $R^1$, $R^2$, Z and n are as previously described, condensing the carbonyl with hydroxylamine to form the hydroxyimino group; or reductively aminating the carbonyl; or reducing the group to the alcohol; or ketalizing or thioketalizing the carbonyl; or with a Grignard reagent obtaining a homologous alcohol; or j. in a compound of formula I, wherein $A^1$ is a lower alkoxycarbonyl and $R^1$, $R^2$, Z and n are as previously described, converting the lower alkoxycarbonyl group with a Grignard reagent to a ketone or a secondary or tertiary alcohol; or reducing the lower alkoxycarbonyl to an alcohol; or k. in a compound of formula I, alkylating $A^1$ when it is an alcohol function or oxidizing it to a carbonyl; or l. in a compound of formula I reducing $A^1$ when it is a nitrile to an amino group or an aldehyde; or m. in a compound of formula I splitting the ketal or thioketal group defined by $A^1$; or n. in a compound of formula I, when $A^1$ is —CH$_2$—NR$^8$—COR$^5$, hydrolyzing the acyl group and optionally converting the resulting base to a pharmaceutically acceptable acid addition salt.

According to process variant (a), a compound of the formula IIa or IIb is condensed with guanidine. In the compound of the formula IIb, representative of leaving group Y are ether residues, for example, alkoxy groups, such as, methoxy, ethoxy, propoxy or the like; thioether residues, such as, alkylthio groups, or aliphatic, aromatic or heterocyclic amino groups —N(R$^3$,R$^4$), such as, lower alkylamino, benzylamino, arylamino, for example, optionally substituted anilino, naphthylamino, di-lower alkylamino, pyrrolidino, piperidino, piperazino, morpholino or the like. Especially preferred is anilino whose phenyl ring can be optionally, singly or multiply substituted by halo-, lower alkyl- or lower alkoxy-.

The reaction of the compound IIa or IIb with guanidine can be carried out according to known methods (see for example the Belgian Pat. Nos. 594,131, 671,982 and 746,846), for instance, in a solvent, for example, an alkanol, such as methanol or ethanol, or in dimethylformamide, dimethylsulfoxide, N-methylpyrazolone, at a temperature in the range of between about 25° and about 200°, preferably at a range of from about 50° to about 170°C.

The compound of the formula IIb, under the foregoing reaction conditions, can be formed in situ from a tautomeric compound of the formula

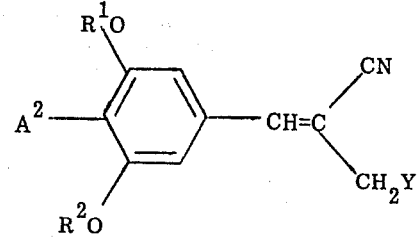

IIc wherein $R^1$, $R^2$, $A^2$ and Y are as hereinbefore described.

The compounds obtained according to process variant (a) are characterized by the formula

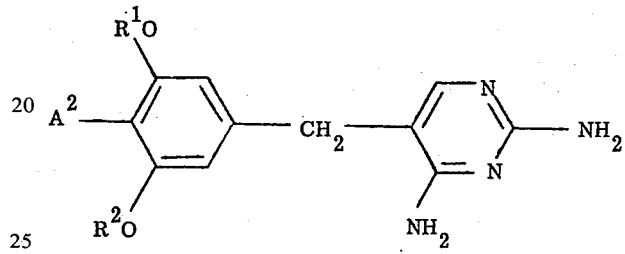

Ib wherein $R^1$, $R^2$ and $A^2$ are as hereinbefore described.

The dehydration of an acid amide of formula III, process variant (b), can be carried out by the use of a dehydrating agent, such as, phosphorus oxychloride, thionylchloride, phosphorus pentoxide or polyphosphoric acid. The reaction can be carried out in an inert organic solvent, for example, pyridine, or an excess of the dehydrating agent itself can also serve as the solvent.

The compounds obtained according to process variant (b) can be characterized by the formula

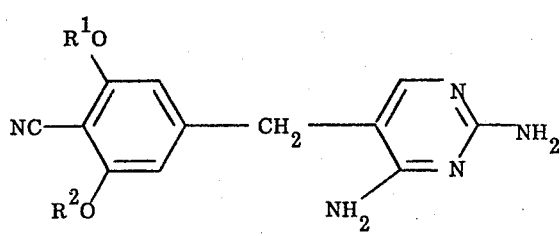

Ic wherein $R^1$ and $R^2$ are as hereinbefore described.

According to process variant (c), a compound of the formula IV is reacted with ammonia, whereby the substituent X' in the pyrimidine residue of the molecule is replaced by an amino group. The reaction is conveniently carried out in alkanolic, for example, methanolic, solution, for instance methanolic ammonia is used as the reaction medium. The reaction temperature conveniently is in the range of from about 80° to about 200°C., preferably between about 100° to about 150°C. Since these temperatures lie above the boiling point of methanol, the reaction is carried out in a closed system, for example, in an autoclave.

There are thus obtained, according to process variant (c), compounds of the formula

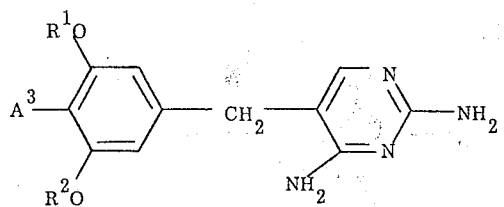 Id

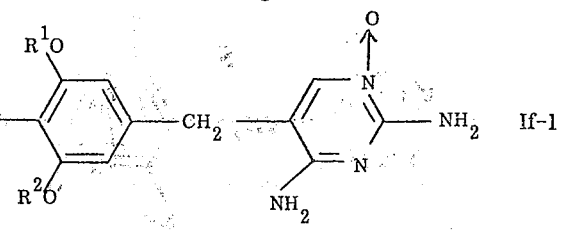 If-1 or

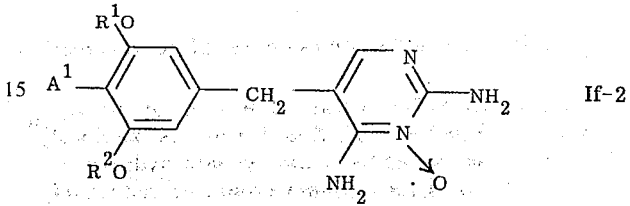 If-2 wherein $R^1$, $R^2$ and $A^1$ are as hereinbefore described.

wherein $A^3$, $R^1$ and $R^2$ are as hereinbefore described.

In process variant (d), the exchange of bromine or chlorine in the compound V for a hydrogen atom can be effected by treatment with reducing agents, such as, hydrogen iodide or catalytically activated hydrogen, for example, palladium in alcohol, or with zinc/glacial acetic acid. When X'' is hydroxy, the compound is first reacted with bromocyanide in the presence of triethylamine and then hydrogenated in the presence of palladium/carbon, whereby the compound of formula Id is obtained.

The splitting of the sulfonyl or sulfoxide group in a compound of formula VI, process variant (e), can be effected by the use of aluminum amalgam in tetrahydrofuran/water, optionally with warming, or by means of a zinc/ethyl acetate mixture.

The compounds thus obtained according to process variant (e) correspond to the formula

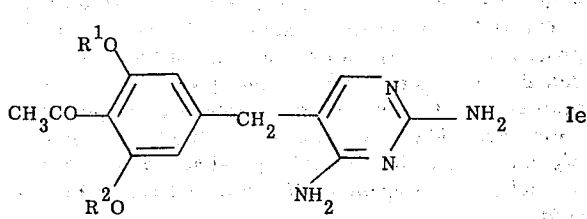 Ie wherein $R^1$ and $R^2$ are as hereinbefore described.

The N-oxidation of process variant (f) can be carried out according to known methods utilizing the usual N-oxidizing agents; particularly preferred are perbenzoic acids and most preferred is m-chloroperbenzoic acid.

The N-oxidation can be carried out, for instance, in inert solvents, for example, chlorinated hydrocarbons, such as chloroform, methylene chloride, or, in alcohols, such as methanol or ethanol, or in dimethylformamide, dimethylsulfoxide, water or also in dioxane. The reaction temperature conveniently lies in the range of from about room temperature to about the boiling point of the solvent, that is, between about 10° and about 60°C. The range of approximately 10° to approximately 20°C. is preferred.

The N-oxides obtained can be isolated from the reaction mixture in the usual manner. When using m-chloroperbenzoic acid or perbenzoic acid as the N-oxidizing agent, it is desirable to shake the reaction mixture out with a weakly alkaline aqueous solution, for example, with aqueous sodium bicarbonate solution, and to make the aqueous extract obtained first acidic in order to precipitate the excess acid and, after removing the latter by filtration, to make the filtrate neutral or weakly basic.

The N-oxidation usually leads to mixtures of $N_1$- and $N_3$- oxides of the formulas The separation and purification of these isomeric reaction products can be effected by chromatography, for example, column chromatography, and/or recrystallization, preferably from polar solvents, such as, alcohols, water or the like.

In the compound of the formula VII which is used as the starting material in process variant (g), X is an amino protecting group which can be converted to the free amino group by hydrolysis or hydrogenolysis. Representative examples of the first category of protecting groups are acyl groups, for example, alkanoyl groups such as formyl, acetyl, propionyl, or the like; or aroyl groups such as benzoyl; tert. butyloxycarbonyl; or the like. A group which can be converted into a free amino group by hydrogenolysis is, for example, carbobenzoxy. The preferred amino protecting groups are acyl groups, most preferably the acetyl group.

The hydrogenolysis of an amino protecting group can be carried out, for example, catalytically, such as by means of palladium on carbon and in a solvent, for example, an alcohol such as methanol, at a temperature in the range of from about 10° to about 50°, preferably at room temperature.

The hydrolysis of a compound of formula VII can be carried out in alkaline medium, for example, with aqueous or aqueous/alcoholic methanolic alkali, or in an acidic medium, for example, with aqueous or aqueous-/alcoholic mineral acids, such as hydrochloric acid or the like.

The esterification of the carboxyl group in a compound of formula Ig can be carried out in a known manner by the reaction of a reactive acid derivative with an alcohol in the presence of a condensing agent, such as an alkali alkoxide, or a strong acid, such as hydrochloric acid. The reduction of the carboxyl group to an aldehyde, according to process variant (h), can be carried out, for example, with a complex metal hydride via the acid chloride.

The reduction of a carbonyl group, according to process variant (i), can be carried out with a complex metal hydride, such as sodium borohydride, in an aqueous alkanol. The reductive amination can be carried out with an amine and Raney-nickel in an inert solvent, for example, ethanol.

The reduction of a lower alkoxy-carbonyl group to a hydroxymethyl group in accordance with process variant (j) can be carried out with diisobutylaluminum hydride in dioxane.

The oxidation of an alcohol group in accordance with process variant (k) can be carried out in an oxidizing agent such as chromium trioxide in pyridine. The reduction of a nitrile group in accordance with process variant (l) can be carried out with a complex metal hydride, such as lithium aluminum hydride in ether (for preparing a compound of formula I wherein A' is —CH$_2$NH$_2$) or with diisobutylaluminum hydride in dioxane (for preparing a compound of formula I wherein A' is —CHO).

The ketal or thioketal cleavage in accordance with process variant (m) can be effected with aqueous acid, optionally with warming, the thioketal cleavage is preferably carried out with a Hg$^{2+}$ salt.

For the hydrolysis in accordance with process varient (n) it is preferably carried out in the presence of an aqueous or aqueous/alcoholic mineral acid.

The starting materials used in the process variants (a) to (e) can be prepared, insofar as they are not known or described in the following table, in analogy to the procedures described in the Examples or according to the methods given in the following table.

used for this purpose, such as hydrochloric acid, sulfuric acid, phosphoric acid or the like, or organic acids, such as formic acid, acetic acid, succinic acid, lactic acid, citric acid, maleic acid, fumaric acid, tartaric acid, methanesulfonic acid, p-toluenesulfonic acid or the like.

The compounds of formula I and their salts are antibacterially active. More particularly, they block the bacterial dihydrofolate reductase and potentiate the antibacterial action of sulfonamides, such as, sulfisoxazole, sulfadimethoxine, sulfamethoxazole, 4-sulfanilamido-5,6-dimethoxypyrimidine, 2-sulfanilamido-4,5-dimethylpyrimidine or sulfaquiloxaline, sulfadiazine, sulfamonomethoxine, iso-sulfisoxazole and other inhibitors for enzymes which are concerned with the folic acid biosynthesis such as, for example, pteridine derivatives.

For such use, one or more of the compounds of formula I and a sulfonamide can be utilized orally, rectally and parenterally, for example, by incorporating a therapeutic dosage in a conventional dosage form, such as tablets, capsules, elixirs, suspensions, solutions or the like. They can be administered in mixture with conventional pharmaceutical carriers or excipients, such as, for example, corn starch, calcium stearate, magnesium

TABLE

| Starting Material | Prepared From | Reaction | Literature |
|---|---|---|---|
| IIb | (structure) | Isomerisation Alkanol and alkali metal alkoxide | Belgian Patent Specification No. 671,982 |
| IIa | IIb | Alcohol addition | |
| IIb IIc | (structure) | Condensation in a strongly alkaline medium | Belgian Patent Specifications Nos. 594,131; 746,846 |
| IV | (structure) | Halogenation | Belgian Patent Specification No. 565,002 |
| IV | (structure) | 1) Condensation with guanidine in an alkaline medium 2) Exchange of the hydroxyl for Br or Cl with phosphorus (oxy) halides | DOS 2,003,578 |

For the preparation of acid addition salts, particularly of salts usable in pharmaceutical preparations, that is, pharmaceutically acceptable acid addition salts, there come into consideration inorganic acids normally carbonate, calcium silicate, dicalcium phosphate, talc, lactose and the like. Moreover, they can be administered in the presence of buffers, or agents used to adjust to isotonicity, and the pharmaceutical dosage forms can, if desired, be subjected to conventional pharmaceutical expedients such as, for example, sterilization. The ratio of a compound of formula I to sulfonamide can vary within a wide range, for example, in the range of 1:40 (parts by weight) to 5:1 (parts by weight); preferred ratios are 1:1 to 1:5.

Thus, for example, a tablet can contain 80 mg. of a compound of formula I and 400 mg. of sulfamethoxazole, or it can contain 20 mg. of a compound of formula I and 100 mg. of sulfamethoxazole. A syrup can contain (per 5 ml.) 40 mg. of a compound of formula I and 200 mg. of sulfamethoxazole.

The compounds of formula I are distinguished by a good tolerance and low toxicity.

The following Examples further illustrate the invention. All temperatures are in degrees Centigrade, unless otherwise mentioned.

EXAMPLE 1

Preparation of α-(2,4-diamino-5-pyrimidinyl-2,6-dimethoxy-p-toluic acid methyl ester 8 G. of sodium metal were dissolved in 200 ml. of absolute methanol in a 2 liter flask having a magnetic stirrrer and a reflux condenser under exclusion of moisture.

24.7 G. of guanidine hydrochloride were added to this solution and the suspension stirred at room temperature for 30 minutes. The formed sodium chloride was removed by filtration under vacuum and washed with about 10 ml. of cold absolute methanol. The filtrate was treated with 46 g. of 4-(3-anilino-2-cyanoallyl)-2,6-dimethoxy-benzoic acid methyl ester and 1000 ml. of isopropanol and the suspension heated at reflux with stirring for 50 hours. The reaction mixture was concentrated, cooled and the precipitated crystals removed by filtration under vacuum.

After crystallization from about 4 liters of methanol with addition of about 1 g. of charcoal, α-(2,4-diamino-5-pyrimidinyl-2,6-dimethoxy-p-toluic acid methyl ester of m.p. 250°-251° was obtained.

The starting material was prepared as follows:

A mixture of 271 g. of 2,6-dimethoxyterephthalic acid 1-monomethyl ester, 1.2l. of absolute benzene, 100 ml. of thionyl chloride and 30 ml. of dimethylformamide was boiled at reflux under exclusion of moisture for 2 hours. The solution was evaporated to dryness in vacuo and the residue dissolved two times in about 100 ml. of absolute benzene and the solvent again removed in vacuo. After recrystallization from 7 l. of hot n-heptane, the residue produced 260 g. of 2,6-dimethoxyterephthalic acid chloride of m.p. 100°-101°C. After concentration of the mother liquors, an additional 20 g. of 2,6-dimethoxyterephthalic acid chloride was obtained (m.p. 90°-95°).

40 G. of 2,6-dimethoxyterephthalic acid chloride were dissolved in 400 ml. of xylene dried over sodium. Under an atmosphere of nitrogen, 4 g. of 5% lead/-barium sulfate and 0.4 ml. of quinoline-sulfur-regulator were added. Thereafter, the suspension was bubbled through with nitrogen for an additional 10 minutes and then hydrogen was led through with stirring at 110°. The course of the reaction was followed by titration of the resulting hydrochloric acid. After about 2 hours (90% of the theoretical amount of hydrochloric acid liberated), the reaction was stopped. The suspension was cooled under nitrogen and the catalyst was removed by filtration under vacuum. Thereafter, the filtrate was concentrated to dryness in vacuo, and the residue taken up in 150 ml. of benzene and shaken with 500 ml. of about 37% sodium bisulfite solution for 2 hours. The benzene phase was separated and the aqueous phase washed with 100 ml. of benzene.

The remaining aqueous solution was cooled to 5° and subsequently adjusted to about a pH of 10 with about 20% sodium hydroxide solution. The precipitated aldehyde and inorganic salts were removed by filtration under vacuum. The solid material was taken up in 400 ml. of benzene and 700 ml. of water. The benzene solution separated and the aqueous phase extracted two times with 100 ml. of benzene each time. The combined benzene extracts were washed with 2 × 50 ml. of water, dried over magnesium sulfate and evaporated to dryness in vacuo to yield 2,6-dimethoxy-4-formylbenzoic acid methyl ester, m.p. 113°-114°.

From a solution of 0.9 g. of sodium metal in 15 ml. of absolute methanol, the solvent was evaporated under an atmosphere of nitrogen and exclusion of moisture. The remaining sodium methylate was suspended in a solution of 25.2 g. of β-morpholinopropionitrile in 28 ml. of dimethylsulfoxide (dried over molecular sieves) and warmed to 70°. At this temperature, a solution of 30 g. of 2,6-dimethoxy-4-formylbenzoic acid methyl ester in 45 ml. of anhydrous dimethylsulfoxide was added dropwise within 30 minutes and subsequently the mixture was stirred at 75° for an additional 30 minutes. After this time, practically no more aldehyde could be detected. The solution was cooled to +5° and treated dropwise with about 30-40 ml. of water, seeded and stirred for about an additional 3 hours. The crystalline product was removed by filtration under vacuum, washed with about 15 ml. of methanol cooled to 0° and recrystallized from methanol.

The 4-(2-cyano-3-morpholinoallyl)-2,6-dimethoxybenzoic acid methyl ester has a m.p. of 137°-138°.

8.6 G. of aniline were treated under cooling with 7.6 ml. of concentrated hydrochloric acid. Subsequently, 32 g. of 4-(2-cyano-3-morpholinoallyl)-2,6-dimethoxybenzoic acid methyl ester and 100 ml. of isopropanol were added. The suspension was heated at reflux with stirring for 30 minutes. About ⅓ to half of the solvent was evaporated and 20 ml. of water added. The resulting crystalline product was removed by filtration under vacuum, washed with a little cold methanol and dried. Recrystallization from methanol yielded 4-(3-anilino-2-cyanoallyl)-2,6-dimethoxybenzoic acid methyl ester of m.p. 193°-194°.

EXAMPLE 2

Preparation of α-(2,4-diamino-5-pyrimidinyl)-2,6-dimethoxy-p-toluic acid methyl ester A solution of 30 mg. of sodium metal in 3 ml. of absolute methanol was treated with 0.12 g. of guanidine hydrochloride, and the suspension was stirred for 15 minutes. 0.29 G. of 4-(3,3-dimethoxy-2-cyanopropyl)-2,6-dimethoxybenzoic acid methyl ester were added and the mixture heated at reflux for 18 hours. Thereafter, the methanol was evaporated in vacuo, and the basic products dissolved in 1N acetic acid. The solution was filtered, made alkaline with concentrated ammonia under cooling. The α-(2,4-diamino-5-pyrimidinyl)-2,6-dimethoxy-p-toluic acid methyl ester was removed by filtration under vacuum and recrystallized from methanol, m.p. 247°–248°.

The starting material was prepared as follows:

11.2 G. of 2,6-dimethoxy-4-formylbenzoic acid methyl ester were added under nitrogen to a solution of 3.45 g. sodium metal in 47 ml. of absolute methanol cooled to 5°. With strong stirring, a solution of 6.6 ml. of acrylonitrile in 3 ml. of methanol was then added dropwise over a period of 20 minutes in such a manner that the temperature did not rise over 20°. The reaction mixture was stirred at room temperature for 17 hours and evaporated to dryness. The residue was taken up in 200 ml. of water and 200 ml. of ether, and the aqueous phase was extracted several times with ether. The ether extracts were dried and concentrated (10 g.). Column chromatography (400 g. of silica gel; eluant; ether) yielded 4-(3,3-dimethoxy-2-cyanopropyl)-2,6-dimethoxybenzoic acid methyl ester, m.p. 90°–92° (from methanol).

EXAMPLE 3

Preparation of
α-(2,4-diamino-5-pyrimidinyl)-2,6dimethoxy-p-toluic acid sodium salt 5.4 G. of guanidine carbonate were added under an atmosphere of nitrogen to a solution of 0.7 g. of sodium metal in 9 ml. of absolute methanol. The suspension was stirred at 80° for 30 minutes and, after cooling to room temperature, it was treated with a solution of 3.5 g. of 4-(2-cyano-3-morpholinoallyl)-2,6-dimethoxybenzoic acid methyl ester in 12 ml. of dimethylsulfoxide.

The mixture was stirred under an atmosphere of nitrogen for 3 hours at 145° and for 2 hours at 175°. Thereafter, the mixture was cooled and poured onto a small amount of ice, filtered and the filtrate evaporated to dryness under high vacuum (temperature < 60°C.). The residue was suspended in ethanol with warming and filtered under vacuum: α-(2,4-diamino-5-pyrimidinyl)-2,6-dimethoxy-p-toluic acid sodium salt, m.p. > 300°.

EXAMPLE 4

Preparation of
α-(2,4-diamino-5-pyrimidinyl)-2,6-dimethoxy-p-toluic acid

A suspension of 12.7 g. of α-(2,4-diamino-5-pyrimidinyl)-2,6-dimethoxy-p-tolylbenzoic acid methyl ester in a solution of 1.7 g. of sodium hydroxide in 80 ml. of water and 20 ml. of ethanol was heated at reflux with stirring for 16 hours. The resulting solution was filtered warm and adjusted to pH 6 with about 40 ml. of 1H hydrochloric acid. The suspension was diluted with 300 ml. of water and filtered, whereby there was obtained: α-(2,4-diamino-5-pyrimidinyl)-2,6-dimethoxy-p-toluic acid, m.p. 264°–267°C. (from methanol/water).

EXAMPLE 5

Preparation of
α-(2,4-diamino-5-pyrimidinyl)-2,6-dimethoxy-p-toluic acid isopropyl ester 1.2 G. of α-(2,4-diamino-5-pyrimidinyl)-2,6-dimethoxy-p-toluoylbenzoic acid methyl ester were added to a solution of 20 mg. of sodium metal in 200 ml. of absolute isopropanol.

The suspension was heated at 150° (5 atmospheres) in a pressure tube for 72 hours. The solution was cooled and evaporated. The remaining substance was suspended in a small amount of water, filtered under vacuum and recrystallized from isopropanol, whereby there was obtained α-(2,4-diamino-5-pyrimidinyl)-2,6-dimethoxy-p-toluic acid isopropyl ester, m.p. 209°–213°.

EXAMPLE 6

Preparation of
α-(2,4-diamino-5-pyrimidinyl)-2,6-dimethoxy-p-toluic acid isopropyl ester A solution of 0.4 g. of sodium metal in 20 ml. of absolute isopropanol was evaporated to dryness. The residue was dissolved in 10 ml. of dimethylsulfoxide. 2 G. of α-(2,4-diamino-5-pyrimidinyl)-2,6-dimethoxy-p-toluic acid methyl ester were added and the reaction mixture stirred under an atmosphere of nitrogen and exclusion of moisture for 24 hours. After the addition of 30 ml. of water, the precipitated α-(2,4-diamino-5-pyrimidinyl)-2,6-dimethoxy-p-toluic acid isopropyl ester was removed by filtration under vacuum and recrystallized from isopropanol.

EXAMPLE 7

Preparation of
α-(2,4-diamino-5-pyrimidinyl)-2,6-dimethoxy-p-toluic acid butyl ester 1.6 G. of α-(2,4-diamino-5-pyrimidinyl)-2,6-dimethoxy-p-toluic acid methyl ester were dissolved in a solution of 20 mg. of sodium metal in 250 ml. of anhydrous butanol-(1). The reaction mixture was boiled at reflux, moisture being excluded for 12 hours, and subsequently filtered hot. The filtrate was evaporated and the residue recrystallized from butanol-(1), whereby there was obtained α-(2,4-diamino-5-pyrimidinyl)-2,6-dimethoxy-p-toluic acid butyl ester, m.p. 186°–188°.

EXAMPLE 8

Preparation of
α-(2,4-diamino-5-pyrimidinyl)-2,6-dimethoxy-p-toluic acid ethyl ester 2.0 G. of α-(2,4-diamino-5-pyrimidinyl)-2,6-dimethoxy-p-toluic acid methyl ester were added to a solution of about 100 mg. of sodium metal in 200 ml. of absolute ethanol. The solution was heated at reflux for 48 hours and filtered. The filtrate was concentrated to 1/4 and cooled. The precipitated α-(2,4-diamino-5-pyrimidinyl)-2,6-dimethoxy-p-toluic acid ethyl ester was removed by filtration under vacuum and recrystallized from ethanol, m.p. 201°–202°.

EXAMPLE 9

Preparation of
4-[(2,4-diamino-5-pyrimidinyl)-methyl]-2,6-dimethoxybenzyl alcohol 135 Ml. of about 15% diisobutylaluminum hydride solution in dioxane were added dropwise within 30 minutes at 50°C. under nitrogen and exclusion of moisture to a solution of 4.45 g. of α-(2,4-diamino-5-pyrimidinyl)-2,6-dimethoxy-p-toluic acid methyl ester in 400 ml. of absolute dioxane. The resulting suspension was stirred at 50° for 1 hour. After cooling to 30°C., the reaction mixture was treated with a mixture of 25 ml. of methanol, 5 ml. of water and 50 ml. of dioxane and stirred at 50° for an additional 2 hours. The solid material was separated and rejected, and the filtrate was evaporated to dryness. After recrystallization from about 20 ml. of methanol, the residue yielded 4-[(2,4-diamino-5-pyrimidinyl)-methyl]-2,6-dimethoxybenzyl alcohol having a m.p. of 227°–228°.

EXAMPLE 10

Preparation of
α-(2',4'-diamino-5'-pyrimidinyl)-2,6-dimethoxy-p-toluic acid methyl ester 3'-oxide and
α-(2',4'-diamino-5'-pyrimidinyl)-2,6-dimethoxy-p-toluic acid methyl ester 1'-oxide A suspension of 3.18 g. of α-(2,4-diamino-5-pyrimidinyl)-2,6-dimethoxy-p-toluic acid methyl ester in 50 ml. of dioxane was treated under stirring with 2.4 g. of 3-chloroperbenzoic acid. After 5 minutes, the oxidizing agent no longer detectable, an additional 1.2 g. of 3-chloroperbenzoic acid were added. After 30 minutes, the brown-colored solution (no peroxide; no oxidizing agent) was evaporated to dryness and the residue treated with 200 ml. of a mixture of chloroform/propanol/concentrated ammonia (80:20:2). The precipitated ammonium salt of the chlorobenzoic acid (about 3.5 g.) was separated, washed with chloroform and the solvent removed in vacuo. The residue (about 3.0 g.) was chromatographed on 90 g. of silica gel with the aforementioned system. The rapidly moving α-(2',4'-diamino-5'-pyrimidinyl)-2,6-dimethoxy-p-toluic acid methyl ester 3'-oxide was recrystallized from methanol, m.p. 251°–253°.

The slowly moving α-(2',4'-diamino-5'-pyrimidinyl)-2,6-dimethoxy-p-toluic acid methyl ester 1'-oxide (Rf~0.1) was recrystallized from methanol, m.p. 258°–259° (decomp.).

EXAMPLE 11

Preparation of
α-(2,4-diamino-5-pyrimidinyl)-2,6-diethoxy-p-toluic acid ethyl ester A solution containing 735 mg. of sodium in 100 ml. of absolute alcohol are reacted with 5.8 g. of guanidine carbonate and 4.2 g. of 4-(3-anilino-2-cyanoallyl)-2,4-diethoxy-benzoic acid ethyl ester and heated at reflux for 20 hours. The alcohol is evaporated under vacuum. To the residue is added 50 ml. of water and after stirring for 3 hours at 25° the α-(2,4-diamino-5-pyrimidinyl)-2,6-diethoxy-p-toluic acid ethyl ester is removed by suction, washed with water, and recrystallized from alcohol, m.p. 197°–199°.

The starting material was prepared as follows:

A mixture comprising 29.7 g. of 2,6-dihydroxyterephthalic acid, 228 g. of potassium carbonate and 234 g. of ethyl iodide in 500 ml. of absolute dimethylformamide are stirred together at 60° for 18 hours with the exclusion of moisture. The solvent is removed under vacuum at 60°, and the residue taken up in 750 ml. of water. The resulting emulsion is extracted with 2 portions of 700 ml. each of ethyl acetate. The ethyl acetate phase is washed with 600 ml. of water, dried over magnesium sulfate and evaporated under vacuum. Recrystallization of the residue from cyclohexane, yields 2,6-diethoxy-terephthalic acid diethyl ester, having a m.p. of 104°–105°.

A solution containing 24.8 g. of 2,6-diethoxy-terephthalic acid diethyl ester in 700 ml. of alcohol is reacted with 84 ml. of 1N sodium hydroxide solution over a period of 3 hours at 25° with stirring. The solution is stirred for 70 hours at 25° and subsequently, evaporated to dryness at 40°. The residue is dissolved in 400 ml. of water, and the aqueous solution is extracted with 300 ml. of ether. The ether phase is discarded and the aqueous phase is made acidic with concentrated hydrochloric acid. The precipitated 2,6-diethoxy-terephthalic acid 1-mono-ethyl ester is removed under suction, washed with water, dried and recrystallized from ethyl acetate/cyclohexane, m.p. 142°–144°.

A solution of 20.9 g. of 2,6-diethoxy-terephthalic acid 1-mono-ethyl ester in 100 ml. of thionyl chloride are heated with the exclusion of moisture for 3 hours at reflux and subsequently evaporated to dryness under vacuum. The residue is suspended in 300 ml. of low boiling petroleum ether. After 2 hours at 25°, the 4-(chloroformyl)-2,6-diethoxy-benzoic acid ethyl ester is recovered with suction, washed with petroleum ether and dried, m.p. 73°–74°.

A mixture of 12 g. of 4-(chloroformyl)-2,6-diethoxybenzoic ethyl ester, 1.4 g. of palladium/barium sulfate catalyst (5%) and 0.2 ml. of quinoline sulfur regulator are heated under an atmosphere of nitrogen at 120° with stirring. Thereafter, hydrogen is passed through the reaction mixture at 120° until 90% of the theoretical amount of acid salt is freed. The reduction is stopped, and the suspension under an atmosphere of nitrogen is cooled to 25°. The catalyst is removed by filtration and the filtrate is evaporated to dryness under vacuum, whereby there is obtained 2,6-diethoxy-4-formylbenzoic acid ethyl ester as a colorless oil. A sample after recrystallization from low boiling petroleum ether yields pure 2,6-diethoxy-4-formylbenzoic acid ethyl ester having a m.p. of 45°–46°.

A solution of 10.2 g. of 2,6-diethoxy-4-formylbenzoic acid ethyl ester, 8.4 g. of β-morpholino propionitrile and 4.1 g. of sodium ethylate in 40 ml. of absolute dimethylsulfoxide are stirred at 25° for 20 hours. The solution is treated with 600 ml. of water and extracted with two 500 ml. portions of ethyl acetate. The ethyl acetate portion is washed twice with 200 ml. of water, dried over magnesium sulfate and evaporated under vacuum. The residue is dissolved in 40 ml. of alcohol.

After remaining at 4° for 20 hours, the crystallized 4-(2-cyano-3-morpholinoallyl)-2,6-diethoxy-benzoic acid ethyl ester is removed by suction, washed with alcohol and dried, m.p. 117°–119°.

A solution of 3.7 g. of 4-(2-cyano-3-morpholinoallyl)-2,6-diethoxy-benzoic acid ethyl ester, 1.4 g. of aniline and 1.5 ml. of concentrated hydrochloric acid in 100 ml. of alcohol are heated at reflux for 1 hour and subsequently evaporated to dryness under vacuum. The residue is treated with 50 ml. of water. After stirring for 30 minutes at 25°, the 4-(3-anilino-2-cyanoallyl)-2,6-diethoxy-benzoic acid ethyl ester is removed by suction, washed with water, dried and recrystallized from methylene chloride/alcohol, m.p. 178°–179°.

EXAMPLE 12

Preparation of α-(2,4-diamino-5-pyrimidinyl)-2,6-diethoxy-p-toluic acid ethyl ester A mixture of 1.94 g. of 4-(2-cyano-3-morpholinoallyl)-2,6-diethoxy-benzoic acid ethyl ester, 3.6 g. of guanidine carbonate and 1.36 g. of sodium ethylate in 20 ml. of absolute dimethylsulfoxide are stirred for 20 hours at 120°. After the addition of 200 ml. of water, the mixture is extracted with two 200 ml. portions of ethyl acetate. The ethyl acetate phase is washed twice with 50 ml. of water, dried over magnesium sulfate and evaporated under vacuum. The residue is chromatographed with ethyl acetate/methanol (4:1) on 40 g. of Kieselgel, whereby there is obtained α-(2,4-diamino-5-pyrimidinyl)-2,6-diethoxy-p-toluic acid ethyl ester having a m.p. of 197°–199°.

EXAMPLE 13

Preparation of 4-[(2,4-diamino-5-pyrimidinyl)-methyl]-2,6-diethoxy-α, α-dimethyl-benzyl alcohol A Grignard reagent prepared from 53.5 g. of magnesium and 284 g. of methyl iodide in 500 ml. of absolute ether is treated in the course of 2 hours with stirring and under ice cooling with a solution of 36 g. of α-(2,4-diamino-5-pyrimidinyl)-2,6-diethoxy-p-toluic acid ethyl ester in 2 liters of absolute tetrahydrofuran. The resulting suspension is heated under reflux for 20 hours. The reaction mixture cooled to 25° is carefully decomposed with ice; then, 3 liters of water and 2N sodium hydroxide solution is added to make the reaction mixture strongly alkaline. The resulting precipitate is removed with suction and the filtrate extracted with two 5 liter portions of ethyl acetate. The ethyl acetate phase is washed with two 2 liter portions of water, dried over magnesium sulfate and evaporated to dryness under vacuum. The residue is dissolved in 2 liters of absolute tetrahydrofuran and as described above, again treated with the Grignard reagent prepared from 26.7 g. of magnesium, 142 g. of methyl iodide and 250 ml. of ether. After work-up of the resulting reaction mixture, it is chromatographed with ethyl acetate/methanol (3:1) on 400 g. of Kieselgel, whereby there is obtained 4-[(2,4-diamino-5-pyrimidinyl)-methyl]-2,6-diethoxy-α,α-dimethyl-benzyl alcohol, which after recrystallization from methanol, has a m.p. of 217°–218°.

EXAMPLE 14

Preparation of α-(2,4-diamino-5-pyrimidinyl)-2,6-dimethoxy-p-toluenenitrile

A suspension of 8.0 g. of α-(2,4-diamino-5-pyrimidinyl)-2,6-dimethyloxy-p-toluene amide in 25 ml. of dry pyridine is treated with 4.0 g. of phosphorus dropwise at 20°–30°. After stirring at room temperature for 3 hours, the mixture is poured in 150 ml. of water, the precipitated α-(2,4-diamino-5-pyrimidinyl)-2,6-dimethoxy-p-toluenenitrile is removed with suction, washed with water and recrystallized from dimethylformamide/methanol, m.p. 270°–272°.

The starting material is prepared as follows:

A solution of 195 g. of 2,6-dimethoxy-4-methylbenzamide in 2.5 l. of water and 1.7 l. of pyridine are treated portionwise with 630 g. of potassium permanganate over a period of 1 hour at 80° with stirring. The resulting mixture is heated over 2 hours at reflux. The magnesium dioxide is removed by filtration, and washed with 1 liter of hot water. The filtrate is evaporated to dryness under vacuum. The residue is taken up in 1 liter of water, the starting material is removed, and the filtrate made strongly acid with concentrated hydrochloric acid. The precipitated 3,5-dimethoxy-terephthalic acid amide is removed under suction, washed with water and dried, m.p. > 300°.

A solution of 50 g. of 3,5-dimethoxy-terephthalic acid amide in 500 ml. of methanol is saturated with hydrochloric acid gas, heated for 3 hours under reflux and additional hydrochloric acid, and thereafter evaporated to dryness under reflux. The residue is strongly agitated with 200 ml. of a 5% sodium bicarbonate solution. The solid residue is removed, washed with water and recrystallized from methanol. The resulting 3,5-dimethoxy-terephthalic acid amide ethyl ester has a m.p. of 259°–261°.

A suspension of 2.4 g. of sodium hydride (50% dispersion in oil) and 7.05 g. of dimethylsulfone in 18 ml. of absolute dimethylsulfoxide are heated with the exclusion of moisture and under an atmosphere of nitrogen for 2 hours at 50°. The heating is interrupted and 5.95 g. of 3,5-dimethoxy-terephthalic acid amide methyl ester is introduced whereby the temperature rises to 65°. The mixture is then heated for 1 hour at room temperature and diluted with 100 ml. of water. The aqueous solution is extracted twice with 50 ml. of ethyl acetate, filtered over charcoal and treated with acetic acid to a pH of 6–7. The precipitated 2,6-dimethoxy-4-[(methylsulfonyl)-acetyl]benzamide is recovered with suction, washed with water and recrystallized from dimethylformamide/ether, m.p. 228°–230°.

A suspension of 37 g. of 2,6-dimethoxy-4-[(methylsulfonyl)-acetyl]-benzamide in 50 ml. of ethanol and 155 ml. of water are treated with a solution comprising 1.55 g, of sodium borohydride in 30 ml. of water (under the addition of 0.1 g. of sodium hydroxide). The reaction mixture is stirred at room temperature for 2 hours, cooled with ice and the residue is removed under suction. After recrystallization from dimethylformamide/ethanol, the 4-[1-hydroxy-2-(methyl-sulfonyl)-ethyl]-2,6-dimethoxy-benzamide melts at 258° with decomposition.

A mixture of 3.1 g. of sodium ethylate, 16 g. of 4-[1-hydroxy-2-(methyl-sulfonyl)-ethyl]-2,6-dimethoxy-benzamide and 8.2 g. of β-anilino-propionitrile in 35 ml. of absolute dimethylsulfoxide are stirred for 5 hours under an atmosphere of nitrogen and exclusion of moisture at 50°. The solution is poured into 400 ml. of water and the resulting emulsion is extracted with three portions of 200 ml. of ethyl acetate.

The ethyl acetate phase is washed with water, dried over sodium sulfate and evaporated under vacuum. The residue is recrystallized from dimethyl-formamide/water, whereby there is obtained 4-(3-anilino-2-cyanoallyl)-2,6-dimethoxy-benzamide, having a m.p. of 226°–228°.

A solution of 0.83 g. of sodium and 55 ml. of absolute ethanol are treated with 3.52 g. of guanidine hydrochloride and 4.1 g. of 4'-(3-anilino-2-cyanoallyl)-2,6-dimethoxy-benzamide and heated for 20 hours with stirring under an atmosphere of nitrogen. The resulting mixture is diluted with 100 ml. of water and the ethanol is removed under vacuum. The precipitated α-(2,4-diamino-5-pyrimidinyl)-2,6-dimethoxy-p-toluenea-mide is removed under suction, washed with water and recrystallized from dimethylformamide/methanol, m.p. 288°–290°.

EXAMPLE 15

Preparation of 2,4-diamino-5-(4-aminomethyl-3,5-dimethoxybenzyl)-pyrimidine

A suspension of 1 g. of N-[4-(2,4-diamino-5-pyrimidinyl)-2,6-dimethoxybenzyl]-acetamide in 30 ml. of 1N hydrochloric acid is warmed at 100° for 15 hours, whereby a clear solution is obtained, and subsequently, is evaporated to dryness under vacuum. The residue is dissolved in a little water. The solution is then made alkaline with calcium carbonate and the precipitated 2,4-diamino-5-(4-aminomethyl-3,5-dimethoxybenzyl)-pyrimidine converted to the maleate, has a m.p. of 176°–178° with decomposition.

EXAMPLE 16

Preparation of N-[4-(2,4-diamino-5-pyrimidinyl)-2,6-dimethoxybenzyl]acetamide

A solution of 0.53 g. of sodium in 36 ml. of absolute ethanol is treated with 2.6 g. of guanidine hydrochloride and 3.4 g. of N-[4-(3-anilino-2-cyanoallyl)-2,6-dimethoxybenzyl]-acetamide and heated with stirring for 20 hours under an atmosphere of nitrogen. The ethanol is removed under reduced pressure. The residue is taken up in water, shaken, washed with water and recrystallized from methanol, whereby there is obtained N-[4-(2,4-diamino-5-pyrimidinyl)-2,6-dimethoxybenzyl]-acetamide, having a m.p. of 218°–220°.

The starting material is prepared as follows:

A mixture of 20 g. of 3,5-dimethoxy-terephthalic acid amide and 100 ml. of thionyl chloride are heated under reflux for 1 hour, whereby the solution becomes clear. The reaction mixture is evaporated to dryness under reduced pressure. The residue is dissolved in benzene, the benzene is removed by distillation and the residue is once more dissolved in benzene, and this solution is added to 400 ml. of methanol. This mixture is heated with stirring for 1 hour, evaporated to dryness and the residue is dissolved in benzene, the benzene solution is washed with water, sodium bicarbonate and water, dried and evaporated. Through the recrystallization of the residue from ethanol there is obtained 4-cyano-3,5-dimethoxy-benzoic acid methyl ester, m.p. 151°–153°.

30 G. of 4-cyano-3,5-dimethoxy-benzoic acid methyl ester and 1500 ml. of methanol and 150 ml. of 1N hydrochloric acid is hydrogenated in the presence of 10 g. of palladium-on carbon 10% at room temperature and under atmospheric pressure. In about 5 hours, 2 moles of hydrogen are taken up. The solution is freed of the catalyst by filtration, evaporated to dryness and the residue is taken up in a little water. The solution is thereafter filtered, saturated with solid potassium carbonate and shaken with benzene. From the shaken benzene mixture, is obtained 4-(aminomethyl)-3,5-dimethoxy-benzoic acid methyl ester, which after recrystallization from high boiling petroleum ether has a m.p. of 81°–83°.

9.0 G. of 4-(aminomethyl-3,5-dimethoxy-benzoic acid methyl ester, dissolved in 30 ml. of glacial acetic acid, is added dropwise to 4.1 g. of acetic anhydride and the mixture is heated for 30 minutes on a water bath. The acetic acid is removed by distillation, and the residue is recrystallized from methanol, whereby there is obtained 4-(acetylaminomethyl)-3,5-dimethoxy-benzoic acid methyl ester, m.p. 184°.

A suspension of 2.9 g. of sodium hydride (50% dispersion in oil) and 3.8 g. of dimethylsulfone in 20 ml. of absolute dimethylsulfoxide are stirred together for 2 hours under an atmosphere of nitrogen and the exclusion of moisture at 50°C. The heating is interrupted and 5.34 g. of 4-(acetylaminoethyl)-3,5-dimethoxy-benzoic acid methyl ester is obtained, and thereafter, the temperature rises to 63°. The mixture is then stirred at room temperature for 2 hours and diluted with 200 ml. of water. The aqueous solution is shaken twice with 50 ml. of ethyl acetate, filtered over charcoal, treated with acetic acid to a pH of 6–7 and maintained in a refrigerator overnight. The precipitated N- 2,6-dimethoxy-4-[(methylsulfonyl)-acetyl]-benzyl -acetamide is recovered with suction, washed with water and recrystallized from methanol/water (50:50), m.p. 233°–235°.

A suspension of 9.5 g. of N- 2,6-dimethoxy-4-[(methylsulfonyl)-acetyl]-benzyl -acetamide in 120 ml. of ethanol and 120 ml. of water is treated with a solution of 2.4 g. of sodium borohydride in 30 ml. of water (with the addition of 0.1 g. of sodium hydroxide). The reaction mixture is stirred at room temperature for 3 hours, cooled with ice, poured into 150 ml. of water, and the solid residue removed with suction. After recrystallization from methanol, the N- p-[1-hydroxy-2-(methylsulfonyl)-ethyl]-2,6-dimethoxybenzyl -acetamide melts at 190°.

A mixture of 0.82 g. of sodium methylate, 3.28 g. of N- p-[1-hydroxy-2-methylsulfonyl)-ethyl]-2,6-dimethoxybenzyl -acetamide and 2.2 g. of β-anilino-propionitrile in 13 ml. of absolute dimethylsulfoxide are stirred together under an atmosphere of nitrogen and exclusion of moisture for 5 hours at 50°. After cooling, the solution is poured into 60 ml. of water, and the resulting emulsion is shaken with ethyl acetate. The ethyl acetate solution is washed with water, dried over sodium sulfate and evaporated. The residue is recrystallized from methanol, whereby there is obtained N-[4-(3-anilino-2-cyanoallyl)-2,6-dimethoxy-benzyl]-acetamide, having a m.p. of 216°.

EXAMPLE 17

Preparation of
4'-[(2,4-diamino-5-pyrimidinyl)-methyl]-2',6'-diethoxy-2-(methylsulfonyl)-acetophenone To a solution of 4.5 g. of dimethylsulfone in 10 ml. of absolute dimethyl-sulfoxide are added 4.6 g. of sodium hydride (about 50% suspension) and the mixture is stirred for 2 hours at 60°. Thereafter, there is added in three portions 5.8 g. of α-(2,4-diamino-5-pyrimidinyl)-2,6-diethoxy-p-toluylbenzoic acid ethyl ester, whereby the temperature rises to 65°.

The reaction mixture is stirred for an additional 15 minutes at 60° and after cooling (cooling with ice water) is treated with about 150 ml. of water. The turbid solution is washed with 3 portions 50 ml. each of benzene, and the benzene extract is discarded. The aqueous phase is adjusted with concentrated hydrochloric acid (about 10 ml.) to pH 7–8. The precipitated 4'-[(2,4-diamino-5-pyrimidinyl)-methyl]-2',6'-diethoxy-2-(methylsulfonyl)-acetophenone is recovered with suction and dried at 50° with high vacuum. After recrystallization from water, the acetophenone has a m.p. of 206°–207°.

EXAMPLE 18

Preparation of
2'-[(2,4-diamino-5-pyrimidinyl)-methyl]-2',6'-diethoxy-acetophenone A suspension of 5.8 g. of 4'-[(2,4-diamino-5-pyrimidinyl)-methyl]-2',6'-diethoxy-2-(methylsulfonyl)acetophenone in 50 ml. of 20% aqueous tetrahydrofuran is reduced with 1 g. of amalgamated aluminum at 65° over a period of 4 hours. (The aluminum chips are immersed in a 2% hydrochloric acid solution for 2 minutes, rinsed with methanol, and thereafter used in the reduction.) The reaction mixture is filtered warm, the filtrate is concentrated and adjusted to a pH of 9 with 5% sodium hydroxide. The resulting solution is then shaken with five 50 ml. portions of ethyl acetate. The resulting crude product after column chromatography (200 g. of silica gel, elution solvent comprising chloroform/N-propanol/concentrated ammonium hydroxide, 80:20:1) yields 4'-[(2,4-diamino-5-pyrimidinyl)-methyl]-2',6'-diethoxy-acetophenone, having a m.p. of 229°–231° recrystallized from methanol.

EXAMPLE 19

Preparation of
4'-[(2,4-diamino-5-pyrimidinyl)-methyl]-2',6'-dimethoxy-2-(methylsulfonyl-acetophenone To a solution of 8.8 g. of dimethylsulfone in 20 ml. of dimethylsulfoxide dried over a molecular sieve is added to 11.5 g. of sodium hydride (about a50% suspension), and the mixture is stirred for 2 hours at 60° under an atmosphere of nitrogen. At this temperature, there is added in portions 10 g. of α-(2,4-diamino-5-pyrimidinyl)-2,6-dimethoxy-p-toluic acid methyl ester, whereby the temperature rises to 70°–75°. The reaction mixture is then stirred for an additional 15 minutes at 60° and then cooled. Thereafter, the reaction mixture is treated with 250 ml. of water with cooling under an atmosphere of nitrogen. The turbid solution is washed with three 50 ml. portions of benzene, the benzene portions are discarded. The remaining solution is adjusted to a pH of 7–8 with concentrated hydrochloric acid and shaken with six portions of 200 ml. of ethyl acetate. The resulting extract is dried over magnesium sulfate, concentrated and the residue is maintained under high vacuum for 5 hours, whereby there is obtained 4'-[(2,4-diamino-5-pyrimidinyl)-methyl]-2',6'-dimethoxy-2-(methylsulfonyl)-acetophenone having a m.p. of 223°–225°. A sample dissolved in water and made acidic with concentrated hydrochloric acid after recrystallization from methanol yields 4-[(2,4-diamino-5-pyrimidinyl)-methyl]-2',6'-dimethoxy-2-(methylsulfonyl)-acetophenone hydrochloride, having a m.p. of > 300°.

EXAMPLE 20

Preparation of 4'-[(2,4-diamino-5-pyrimidinyl)-methyl]-2',6'-dimethoxy-acetophenone A solution of 7.0 g. of 4'-[(2,4-diamino-5-pyrimidinyl)-methyl]-2',6'-dimethoxy-2-(methylsulfonyl)-acetophenone in 80 ml. of 20% aqueous tetrahydrofuran is reduced with 1 g. of amalgamated aluminum at 40° over a period of 1 hour. The reaction mixture is filtered and the filtrate is concentrated to ⅓ its original volume and is adjusted to a pH of 9 with 4N sodium hydroxide solution. The precipiated product is taken up in ethyl acetate. The ethyl acetate extracts are dried over magnesium sulfate and evaporated. The residue is recrystallized from methanol and there is obtained 4'-[(2,4-diamino-5-pyrimidinyl)-methyl]-2',6'-dimethoxy-acetophenone, having a m.p. of 282°–285° (with decomposition).

EXAMPLE 21

Preparation of
4-[(2,4-diamino-5-pyrimidinyl)-methyl]-2,6-diethoxy-α-[(methylsulfonyl)-methyl]-benzyl alcohol To a suspension of 1 g. of 4'-[(2,4-diamino-5-pyrimidinyl)-methyl]-2',6'-diethoxy-2-(methylsulfonyl)-acetophenone in a mixture of 25 ml. of ethanol and 10 ml. of water there is added portionwise with stirring over a period of 30 minutes 500 mg. of sodium borohydride. First the solution becomes clear, and after an additional 30 minutes of stirring, there crystallizes 4-[(2,4-diamino-5-pyrimidinyl)-methyl]-2,6-diethoxy-α-[(methylsulfonyl)-methyl]-benzyl alcohol, having a m.p. of 205°–206° after recrystallization from methanol.

EXAMPLE 22

Preparation of
4-[(2,4-diamino-5-pyrimidinyl)-methyl]-2,6-dimethoxy-α-methylbenzyl alcohol A solution of 302 mg. of 4'-(2,4-diamino-5-pyrimidinyl)-methyl-2',6'-dimethoxy-acetophenone in 30 ml. is diluted with 6 ml. of water and to it is added one drop of 1N sodium hydroxide. Thereafter, over a period of 3 hours, there is added in 50 mg portions 200 mg. of sodium borohydride at 40°. About half of the solvent is removed by distillation under vacuum. The precipiated 4-(2,4-diamino-5-pyrimidinyl)-methyl-2,6-dimethoxy-α-methylbenzyl alcohol is recovered with suction and subsequently recrystallized from methanol, m.p. 280°–285° (with decomposition).

EXAMPLE 23

Preparation of
4-[(2,4-diamino-5-pyrimidinyl)-methyl]-2,6-dimethoxy-α-methyl-benzyl alcohol To a guanidine solution in methanol, prepared from 0.34 g. of sodium metal in 40 ml. of methanol and 1.38 g. of guanidine hydrochloride, there is added 4.0 g. of 4-(1-hydroxyethyl)-3,5-dimethoxy-α-(methoxymethylene)-hydro-cinnamic acid nitrile and the mixture is heated at reflux for 18 hours. The solvent is evaporated under normal pressure and the semi-solid residue is separated through column chromatography (100 g. silica gel, with chloroform/n-propanol/concentrated ammonium hydroxide, 80:20:1 as the elution solvent). From a portion of the product containing fraction and recrystallization of the residue from methanol, there is obtained 4-[(2,4-diamino-5-pyrimidinyl)-methyl]-2,6-dimethoxy-α-methylbenzyl alcohol.

The starting material can be prepared as follows:

To a solution containing 8.5 g. of dimethylsulfone and 15 ml. of dimethylsulfoxide there is added 3 g. of about a 50% suspension of sodium hydride and the mixture is stirred for 2 hours under an atmosphere of nitrogen at 60°. Thereafter, there is added dropwise a solution of 9 g. of 2,6-dimethoxy-4-(diethoxy-methyl)-benzoic acid methyl ester in 5 ml. of dimethylsulfoxide and the mixture is heated for an additional 30 minutes at 65°. After cooling, the reaction mixture is dissolved with 100 ml. of water and extracted with five 50 ml. portions of ether. The combined ether phases are dried over magnesium sulfate, evaporated to dryness and the residue, after direct work-up, yields 2,6-dimethoxy-4-(diethoxy-methyl)-methylsulfonyl acetophenone.

A solution of 8.8 g. of sulfone in 80 ml. of 10% aqueous tetrahydrofuran is reduced with 0.8 g. of amalgamated aluminum pieces for 2 hours at 50°C. After this time, there remains no more sulfone. The suspension is filtered and the filtrate is concentrated to ⅔ its original volume and shaken with five 50 ml. portions of ether. After drying of the ether extract and evaporation of the solvent, there is obtained 4-(diethoxymethyl)-2,6-dimethoxy-acetophenone.

To a solution of 4 g. of 4-(diethoxymethyl)-2,6-dimethoxy-acetophenone in 20 ml. of 30% methanol and 1 drop of 4N sodium hydroxide there is added at room temperature with stirring in small portions over a period of 4 hours 1 g. of sodium borohydride. The reaction mixture is stirred for an additional 1 hour. It is concentrated to about ⅓ its original volume and diluted with 30 ml. of water. The resulting suspension is made acid with 2N hydrochloric acid (about pH 1, covered with 50 ml. of ether and stirred at room temperature for another hour. Then, the ether phase is decanted, dried over magnesium sulfate and evaporated. The residue, after crystallization from ether, yields 4-(1-hydroxyethyl)-3,5-dimethoxy-benzaldehyde, having a m.p. of 95°–96°.

In a solution of 0.45 g. of sodium in 200 ml. of methanol there is dissolved 1.94 g. of β-methoxy-propionitrile and 4.0 g. of 4-(1-hydroxyethyl)-3,5-dimethoxy-benzaldehyde and the mixture is heated at reflux for 24 hours. After removal of the solvent, the residue is taken up in 50 ml. of benzene and 10 ml. of water. The benzene phase is separated and again washed with water. The resulting 4-(1-hydroxyethyl)-3,5-dimethoxy-α-(methoxymethylene)-hydrocinnamic acid nitrile (yellow oil) is recovered after removal of the benzene.

The sample, through preparative thin layer chromatography, is obtained and yields 4-(1-hydroxyethyl)-3,5-dimethoxy-α-(methoxymethylene)-hydroxycinnamic acid nitrile as a colorless oil, having a m.p. of <30°.

EXAMPLE 24

Preparation of
4-[(2,4-diamino-5-pyrimidinyl)-methyl]-α-ethyl-2,6-dimethoxy-benzyl alcohol From 3.5 g. of β-(dimethoxymethyl)-3,5-dimethoxy-4-(1-hydroxypropyl)-hydrocinnamic acid nitrile, 2.29 g. of guanidine hydrochloride, 0.56 g. of sodium and 35 ml. of methanol, there is obtained in an analogous manner to that described in Example 23, 4-[(2,4-diamino-5-pyrimidinyl)-methyl]-α-ethyl-2,6-dimethoxy-benzyl alcohol, having a m.p. of 235°–238° from methanol.

The starting material can be prepared as follows:

In a solution comprising 0.18 g. of sodium metal in 50 ml. of absolute methanol there is dissolved 2.74 g. of β-methoxypropionitrile and 4.8 g. of 4-(1-hydroxypropyl)-3,5-dimethoxy-benzaldehyde and heated at reflux for 48 hours. The mixture is evaporated and the residue is taken up in 50 ml. of benzene and 10 ml. of water. The aqeuous phase is washed with two portions of 20 ml. each of benzene. The combined benzene phases are dried and evaporated. The residue (the yellow oil) is used in this form. A sample obtained through preparative thin layer chromatography (silica gel ether as the elution solvent) yields α-(dimethoxymethyl)-3,5-dimethoxy-4-(1-hydroxypropyl)-hydrocinnamic acid nitrile as a colorless oil.

EXAMPLE 25

Preparation of
2,4-diamino-5-[3,5-dimethoxy-4-(methoxymethyl)-benzyl]-pyrimidine To a solution comprising 0.62 g. of sodium metal in 50 ml. of methanol there is added 2.3 g. of guanidine hydrochloride and the suspension is stirred for 30 minutes. The formed sodium chloride is removed with suction and washed with a little cold methanol. The filtrate is added to a solution of 5.0 g. of α-(dimethoxymethyl)-3,5-dimethoxy-4-(methoxymethyl)-hydrocinnamic acid nitrile in 20 ml. of methanol and heated at reflux for 2 hours. Thereafter, the methanol is removed by distillation, (the inner temperature being up to 80°). The residue is treated with 25 ml. of isopropanol and subsequently evaporated over a period of 2 hours. The residue is subjected directly to chromatographic separation (10 g. silica gel, elution solvent chloroform/N-propanol/ammonia 80:20:1) whereby there is obtained 2,4-diamino-5-[3,5-dimethoxy-4-(methoxymethyl)-benzyl]-pyrimidine, having a m.p. of 221°–223° from methanol.

The starting material was prepared as follows:

A solution of 29.8 g. of 2,6-dimethoxy-4-(α,α-diethoxymethyl)-benzoic acid methyl ester was dissolved in 250 ml. of absolute benzene and treated at 25°–40°C. with 230 ml. of about a 20% solution of diisobutyl-aluminum hydride in toluene. The homogeneous mixture was stirred at room temperature for 3 hours and then taken up with a solution of 10 ml. of water, 25 ml. of methanol and about 10 ml. of benzene while cooling in such a manner that the temperature did not exceed 40°C. The resulting suspension was stirred for an additional 30 minutes. The aluminum hydroxide was removed by filtration with suction, washed with benzene and the filtrate evaporated to dryness, whereby there was obtained 2,6-dimethoxy-4-α,α-diethoxy-benzyl alcohol as a colorless viscous oil.

After treatment of the foregoing oil with 20 ml. of 1N hydrochloric acid and crystallization from benzene, there was obtained crystalline α-hydroxy-3,5-dimethoxy-p-tolualdehyde, having a m.p. of 128°–129°C. (sublimation).

A solution of 20 g. of 2,6-dimethoxy-4-α,α-diethoxy-benzyl alcohol in 40 ml. of absolute ether was added dropwise to a suspension of 2.35 g. of sodium hydride (55%) in 40 ml. of absolute ether. The mixture was stirred under an atmosphere of nitrogen at room temperature for 1 hour, and then treated with 40 g. of methyl iodide and stirred at reflux for 22 hours. The solvent and excess methyl iodide were removed by distillation. The residue was treated with 100 ml. of 1N hydrochloric acid at 25°C. over a period of 15 minutes and the resulting aldehyde was taken up in ether. Recrystallization from benzene/n-pentane yields α,3,5-trimethoxy-p-tolualdehyde, having a m.p. of 72°–76°C.

2.45 G. of β-methoxy-propionitrile and 5 g. of α,3,5-trimethoxy-tolualdehyde were dissolved in a solution of 0.25 g. of sodium metal in 20 ml. of absolute methanol and the resulting mixture was boiled at reflux for 48 hours. No aldehyde could be detected after this time. After evaporation of the solvent, the residue was taken up in 50 ml. of benzene and 15 ml. of water. The benzene phase was separated, washed several times with water, dried over magnesium sulfate and evaporated, whereby there was obtained a yellowish oil which was used in the process described in the first paragraph of this Example with no further working-up.

An analytical sample was purified by chromatography on silica gel using ether as the eluant, whereby there was obtained α-(dimethoxymethyl)-3,5-dimethoxy-4-(methoxymethyl)-hydrocinnamic acid nitrile as a colorless crystalline substance, having a m.p. of about 30°.

EXAMPLE 26

Preparation of
4-[(2,4-diamino-5-pyrimidinyl)-methyl]-2,6-dimethoxy-α,α-dimethyl-benzyl alcohol A suspension of 11.3 g. of N- 2-amino-5-[4-(1-hydroxy-1-methyl-ethyl)-3,5-dimethoxy-benzyl]-4-pyrimidinyl -acetamide in 40 ml. of 10% methanolic potassium hydroxide was boiled at reflux for 1 hour and then cooled to about 10°C. The crystals were removed by filtration with suction and washed with a small amount of methanol. After crystallization from methanol, there was obtained 4-[(2,4-diamino-5-pyrimidinyl)-methyl]-2,6-dimethoxy-α,α-dimethyl-benzyl alcohol having a m.p. of 248°–250°C.

The starting material was prepared as follows:

5 G. of α-(2,4-diamino-5-pyrimidinyl)-2,6-dimethoxy-p-toluic acid methyl ester were added portionwise to 10 ml. of hot (95°C) acetic anhydride. The resulting solution was stirred for an additional 30 minutes at 95°C. and then treated with 30 ml. of toluene and cooled. The formed α-(2,4-diacetamido-5-pyrimidinyl)-2,6-dimethoxy-p-toluic acid methyl ester was removed by filtration with suction and recrystallized from methanol; m.p. 183°–185°C.

A solution of 2.5 g. of α-(2,4-diacetamido-5-pyrimidinyl)-2,6-dimethoxy-p-toluic acid methyl ester in 200 ml. of absolute tetrahydrofuran was added dropwise over a period of 30 minutes to a methylmagnesium iodide solution prepared from 2.4 g. of magnesium and 14.5 g. of methyl iodide in 100 ml. of ether. The resulting suspension was stirred at 40°C. for 24 hours. The mixture was treated with 20 ml. of water. The organic phase was separated, washed with a small amount of 4N sodium hydroxide and water, dried over magnesium sulfate and evaporated. The crude product thus obtained, a yellowish oil, was used in the process described in the first paragraph of this Example without further working-up.

A sample was subjected to chromatographic purification on silica gel using chloroform/n-propanol/concentrated ammonia (80:20:1) as the eluant, whereby there was obtained N- 2-amino-5-[4-(1-hydroxy-1-methyl-ethyl)-3,5-dimethoxy-benzyl]-4-pyrimidinyl -acetamide, having a m.p. of 214°–216°C. (from methanol).

EXAMPLE 27

Preparation of
4-[(2,4-diamino-5-pyrimidinyl)-methyl]-2,6-dimethoxy-α,α-dimethyl-benzyl alcohol 21.1 G. of guanidine hydrochloride were added to a solution of 5.1 g. of sodium metal in 300 ml. of absolute methanol and the resulting suspension was heated at reflux for 15 minutes. After cooling, the sodium chloride was removed by filtration with suction and washed with a small amount of cold methanol. Thereafter, 51.4 g. of 4-(1-hydroxy-1-methyl-ethyl)-3,5-dimethoxy-α-(methoxy-methylene)-hydrocinnamic acid nitrile were dissolved in the filtrate and the mixture was boiled at reflux for 18 hours. After cooling, the mixture was concentrated in vacuo. The residue was suspended in about 50 ml. of methnaol with warming, and again cooled. The formed solid material was removed by filtration with suction and washed with cold methanol. Crystallization from methanol gave 4-[(2,4-diamino-5-pyrimidinyl)-methyl]-2,6-dimethoxy-α,α-dimethyl-benzyl alcohol.

The starting material was prepared as follows:

A solution of 22.4 g. of 2,6-dimethoxy-4-formyl-benzoic acid methyl ester, 17.8 g. of orthoformic acid ethyl ester and 0.5 ml. of concentrated hydrochloric acid in 100 ml. of absolute ethanol was boiled at reflux for 2 hours. The mixture was concentrated under reduced pressure and yielded 2,6-dimethoxy-4-(α,α-diethoxy-methyl)-benzoic acid methyl ester.

A methylmagnesium iodide solution was prepared from 21.6 g. of magnesium and 62 ml. of methyl iodide in 800 ml. of ether. 90 G. of 2,6-dimethoxy-4-(α,α-diethoxy-methyl)-benzoic acid methyl ester in 150 ml. of ether were added dropwise to this Grignard solution at room temperature. After the reaction slowed down, the mixture was boiled at reflux for an additional 3 hours. After cooling, the suspension was treated with 50 ml. of water. Thereafter, 50 ml. of 4N sodium hydroxide were added. The ether phase was separated and washed with 10 ml. of 4N sodium hydroxide. The aqueous-alkaline solution was extracted with five 200 ml. portions of ether and the combined ether extracts were dried over sodium sulfate and evaporated. The residue was shaken well for 10 minutes with 250 ml. of 1N hydrochloric acid and taken up in about 250 ml. of ether. The ether solution was washed with water, dried over magnesium sulfate and concentrated. Crystallization from ether/petroleum ether yielded 4-(1-hydroxy-1-methylethyl)-3,5-dimethoxy-benzaldehyde having a m.p. of 52°–53°C.

From 1.5 G. of sodium in 500 ml. of methanol, 20.8 g. of β-methoxy-propionitrile and 50.0 g. of 4-(1-hydroxy-1-methylethyl)-3,5-dimethoxy-benzaldehyde there was obtained, by heating under reflux for 48 hours and working up, 4-(1-hydroxy-1-methylether)-3,5-dimethoxy-α-(methoxymethylene)-hydrocinnamic acid nitrile as a yellow oil.

An analytical sample was purified by chromatography on silica gel using ether as the eluant; m.p. about 55°C.

EXAMPLE 28

Preparation of 4-[(2,4-diamino-5-pyrimidinyl)-methyl]-α,α-diethyl-2,6-dimethoxy-benzyl alcohol C.

2.96 G. of guanidine hydrochloride were added to a solution of 0.73 g. of sodium metal in 45 ml. of methanol and the resulting suspension was boiled at reflux for 15 minutes. After cooling, the sodium chloride was removed by filtration with suction and 8 g. of 4-(1-hydroxy-1-ethyl-propyl)-3,5-dimethoxy-α-(methoxymethylene)-hydrocinnamic acid nitrile were dissolved in the filtrate. The mixture was boiled at reflux for 24 hours. Thereafter, the solvent evaporated at normal pressure and the residue heated at 100°C for 15 minutes. The resulting semi-solid mixture was purified by column chromatography [200 g. of silica gel; eluant: chloroform/n-propanol/concentrated ammonia (80:20:1)] and yielded, after recrystallization from methanol, 4-[(2,4-diamino-5-pyrimidinyl)-methyl]-α,α-diethyl-2,6-dimethoxy-benzyl alcohol, having a m.p. of 160°–161°C.

The starting material was prepared as follows:

A Grignard reagent was prepared from 2.16 g. of magnesium shavings and 10.3 ml. of ethyl iodide in 280 ml. of absolute ether. 9 G. of 2,6-dimethoxy-4-(diethoxy-methyl)-benzoic acid methyl ester were added to this Grignard reagent, the temperature rising to about 32°C. The mixture was boiled at reflux for 2 hours and then treated with 15 ml. of water and 50 ml. of 4N sodium hydroxide. The aqueous phase was separated and washed five times with 15 ml. of ether each time. The combined ether extracts were washed with water and concentrated to 100 ml. The ether solution was stirred overnight at room temperature with 25 ml. of 1N hydrochloric acid. The ether phase was separated, washed with water, dried over magnesium sulfate and concentrated. The residue, a colorless oil (7.7 g.), was a mixture of two substances which are separated by column chromatography on 650 g. of silica gel using benzene/ether (3:1) as eluant.

The substance with $R_f$ 0.45 in the foregoing system was a colorless oil and was identified as 4-(1-hydroxy-1-ethylpropyl)-3,5-dimethoxy-benzaldehyde.

The slower running compound ($R_f$ 0.30) was a colorless oil and was identified as 4-(1-hydroxypropyl)-3,5-dimethoxy-benzaldehyde.

8G. of 4-(1-hydroxy-1-ethylpropyl)-3,5-dimethoxy-benzaldehyde and 5.4 g. of β-methoxy-propionitrile were added to a solution of 0.44 g. of sodium metal in 40 ml. of absolute methanol. The resulting yellow-brown solution was boiled at reflux for 18 hours. The mixture was then concentrated and the residue taken up in 250 ml. of ether and 100 ml. of water. The ether phase was washed three times with 50 ml. of water each time, dried over magnesium sulfate, evaporated and dried in a high vacuum at 40°C. for 8 hours. The thus-obtained crude product was used in the process described in the first paragraph of this Example without further purification.

A sample was purified by preparative thin-layer chromatography, whereby there was obtained 4-(1-hydroxy-1-ethylpropyl)-3,5-dimethoxy-α-(methoxymethylene)-hydrocinnamic acid nitrile as a colorless oil.

EXAMPLE 29

Preparation of α-(2,4-diamino-5-pyrimidinyl)-2,6-dimethoxy-p-tolyl-benzoic acid methyl ester A solution of 40 mg. of mercuric chloride in 1 ml. of water and 700 mg. of zinc powder was added to a solution of 0.9 g. of α-(2,4-diamino-6-chloro-5-pyrimidinyl)-2,6-dimethoxy-p-toluic acid methyl ester in 12 ml. of glacial acetic acid and the mixture was boiled at reflux and stirred overnight. The mixture was filtered while hot. The zinc powder was washed on the filter with 6 ml. of 90% acetic acid and the combined filtrates were made alkaline while cooling with 20 ml. of concentrated ammonium hydroxide. The precipitated α-(2,4-diamino-5-pyrimidinyl)-2,6-dimethoxy-p-tolyl-benzoic acid methyl ester was removed by filtration with suction and recrystallized from methanol; m.p. 250°–251°C.

The starting material was prepared as follows:

A mixture of 11.2 g. of 2,6-dimethoxy-4-formyl-benzoic acid methyl ester, 6.3 g. of cyanoacetic acid ethyl ester and three drops of piperidine was heated in an open vessel with stirring to 120°C. and stirred at this temperature for an additional 15 minutes. The residue was recrystallized from ethyl acetate and yielded α-cyano-3,5-dimethoxy-4-methoxycarbonyl-cinnamic acid ethyl ester, having a m.p. of 142°–144°C.

A solution of 10.6 g. of α-cyano-3,5-dimethoxy-4-methoxy-carbonyl-cinnamic acid ethyl ester in 500 ml. of ethanol was hydrogenated in the presence of 0.5 g. of palladium-on-carbon (5%) at room temperature and 760 mm. of mercury. After the uptake of an equivalent of hydrogen (810 ml.), the hydrogenation was interrupted. The catalyst and partially precipitated product were removed by filtration with suction and washed on the filter with benzene. The filtrate was evaporated to dryness. The residue was recrystallized from ethyl acetate and yielded α-cyano-3,5-dimethoxy-4-methoxycarbonyl-dihydro-cinnamic acid ethyl ester having a m.p. of 119°–121°C.

8 G. of α-cyano-3,5-dimethoxy-4-methoxycarbonyl-dihydrocinnamic acid ethyl ester were dissolved in a solution of 0.7 g. of sodium metal in 80 ml. of absolute ethanol. The mixture was treated with an ethanolic solution of guanidine prepared from 0.7 g. of sodium in 100 ml. of ethanol and 2.7 g. of guanidine hydrochloride. The mixture was boiled at reflux for 2 hours and then evaporated to dryness. The residue was dissolved in 90 ml. of hot water, filtered and acidified to pH 4 with glacial acetic acid. After recrystallization from methanol, the precipitated product gave α-(2,4- diamino-6-hydroxy-5-pyrimidinyl)-2,6-dimethoxy-p-toluic acid methyl ester having a m.p. of 224°–226°C.

2.4 G. of N,N-dimethyl-aniline were added dropwise with stirring to a suspension of 3.4 g. of α-(2,4-diamino-6-hydroxy-5-pyrimidinyl)-2,6-dimethoxy-p-toluic acid methyl ester in 25.6 g. of phosphorus oxychloride. The resulting mixture was brought to the boiling temperature in the course of 1 hour and then boiled at reflux for 4 hours. Thereafter, two thirds of the phosphorus oxychloride were removed by distillation under reduced pressure. The residue was poured onto 80 g. of ice with stirring and left to stand for two days at room temperature. The suspension was treated with 38 ml. of 25% aqueous ammonia, while the temperature did not exceed 20°C. After 2 hours, the solid material was removed by filtration with suction, rinsed with a small amount of water in a flask and separated from the N,N-dimethyl-aniline with steam. After cooling, the compound in suspension was removed by filtration with suction and taken up in ethyl acetate. The solution was dried over magnesium sulfate and the solvent evaporated. The dark residue (1.6 g.) was purified by column chromatography on 60 g. of silica gel (Merck) using chloroform/n-propanol/25% ammonia (80:20:1) as the eluant, whereby there was obtained α-(2,4-diamino-6-chloro-5-pyrimidinyl)-2,6-dimethoxy-p-toluic acid methyl ester having a m.p. of 228°–229°C. (from methanol).

EXAMPLE 30

Example 30

| Tablet Formulation: | |
|---|---|
| Methyl α-(2,4-diamino-5-pyrimidinyl)-2,6-dimethoxy-p-toluate | 80 mg |
| Sulfamethoxazol | 400 mg |
| Corn Starch | 114 mg |
| Talc | 5 mg |
| Magnesium stearate | 1 mg |
| Total weight | 600 mg |

We claim:
1. A compound of the formula

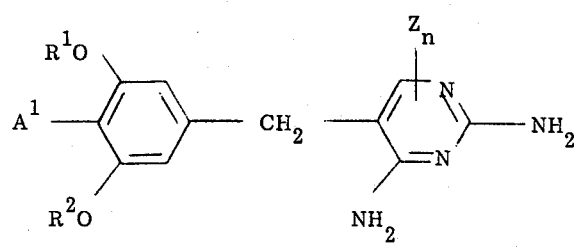

wherein $R^1$ and $R^2$, individually, are lower alkyl of 1 to 4 carbon atoms or lower alkenyl of 2 to 3 carbon atoms; Z is an oxygen atom bonded to one of the cyclic nitrogen atoms, n is 0 or 1, and $A^1$ is trifluoromethyl,

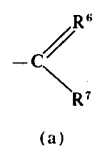 or 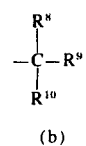

(a)  (b)

wherein $R^6$ is oxo and $R^7$ is hydrogen, lower alkyl of 1 to 4 carbon atoms or alkoxy of 1 to 4 carbon atoms; or $R^6$ is hydroxyimino and $R^7$ is lower alkyl of 1 to 4 carbon atoms; or $R^6$ taken together with $R^7$ is nitrils; $R^8$ and $R^9$, individually, are hydrogen or lower alkyl of 1 to 4 carbon atoms; and $R^{10}$ is hydroxy, lower alkoxy of 1 to 4 carbon atoms or $-N(R^3)(R^4)$, wherein $R^3$ and $R^4$, individually, are hydrogen, lower alkyl of 1 to 4 carbon atoms or lower alkanoyl of 1 to 4 carbon atoms; or $R^9$ and $R^{10}$, individually, are lower alkoxy of 1 to 4 carbon atoms or lower alkylthio of 1 to 4 carbon atoms; or $R^9$ taken together with $R^{10}$ are lower alkylenedioxy of 2 to 3 carbon atoms or lower alkylenedithio of 2 to 3 carbon atoms; or a pharmaceutically acceptable acid addition salt thereof.

2. A compound in accordance with claim 1, wherein n is 0, $R^6$ is oxo and $R^7$ is hydrogen, lower alkyl of 1 to 4 carbon atoms or lower alkoxy of 1 to 4 carbon atoms; $R^8$ and $R^9$, individually, are hydrogen or lower alkyl of 1 to 4 carbon atoms, and $R^{10}$ is hydroxy, lower alkoxy of 1 to 4 carbon atoms or $N(R^3)(R^4)$, wherein $R^3$ and $R^4$, individually, are hydrogen, lower alkyl of 1 to 4 carbon atoms or lower alkanoyl of 1 to 4 carbon atoms.

3. A compound in accordance with claim 1, wherein n is 0, $R^6$ is oxo and $R^7$ is hydrogen, lower alkyl of 1 to 4 carbon atoms or lower alkoxy of 1 to 4 carbon atoms; $R^9$ and $R^{10}$, individually, are lower alkoxy of 1 to 4 carbon atoms or lower alkylthio of 1 to 4 carbon atoms.

4. A compound in accordance with claim 1, wherein n is 0, $R^6$ is oxo and $R^7$ is hydrogen, lower alkyl of 1 to 4 carbon atoms or lower alkoxy of 1 to 4 carbon atoms; $R^9$, taken together with $R^{10}$, are lower alkylenedioxy of 2 to 3 carbon atoms or lower alkylenedithio of 2 to 3 carbon atoms.

5. A compound in accordance with claim 1, wherein n is 0, $R^6$ is oxo and $R^7$ is hydrogen, lower alkyl of 1 to 4 carbon atoms or lower alkoxy of 1 to 4 carbon atoms.

6. A compound in accordance with claim 1, wherein n is 0, $R^6$ is hydroxyimino and $R^7$ is lower alkyl of 1 to 4 carbon atoms; $R^8$ and $R^9$, individually, are hydrogen or lower alkyl of 1 to 4 carbon atoms, and $R^{10}$ is hydroxy, lower alkoxy of 1 to 4 carbon atoms or $N(R^3)(R^4)$, wherein $R^3$ and $R^4$, individually, are hydrogen, lower alkyl of 1 to 4 carbon atoms or lower alkanoyl of 1 to 4 carbon atoms.

7. A compound in accordance with claim 1, wherein n is 0, $R^6$ is hydroxyimino and $R^7$ is lower alkyl of 1 to 4 carbon atoms; $R^9$ and $R^{10}$, individually, are lower alkoxy of 1 to 4 carbon atoms or lower alkylthio of 1 to 4 carbon atoms.

8. A compound in accordance with claim 1, wherein n is 0, $R^6$ is hydroxyimino and $R^7$ is lower alkyl of 1 to 4 carbon atoms; $R^9$, taken together with $R^{10}$, are lower alkylenedioxy of 2 to 3 carbon atoms or lower alkylenedithio of 2 to 3 carbon atoms.

9. A compound in accordance with claim 1, wherein n is 0; $R^6$ is hydroxyimino, $R^7$ is lower alkyl of 1 to 4 carbon atoms and $R^8$ is hydrogen.

10. A compound in accordance with claim 1, wherein $A^1$ is trifluoromethyl.

11. A compound in accordance with claim 1, wherein $R^1$ and $R^2$ are lower alkyl of 1 to 4 carbon atoms and $A^1$ is C-mono-alkylated or dialkylated hydroxymethyl wherein each alkyl is of 1 to 4 carbon atoms.

12. A compound in accordance with claim 1, α-(2,4-diamino-5-pyrimidinyl)-2,6-dimethoxy-p-toluic acid isopropyl ester.

13. A compound in accordance with claim 1, α-(2,4-diamino-5-pyrimidinyl)-2,6-dimethoxy-p-toluic acid methyl ester.

14. A compound in accordance with claim 1, α-(2,4-diamino-5-pyrimidinyl)-2,6-dimethoxy-p-toluic acid.

15. A compound in accordance with claim 1, α-(2,4-diamino-5-pyrimidinyl)-2,6-diethoxy-p-toluic acid ethyl ester.

16. A compound in accordance with claim 1, ethyl-α-(2,4-diamino-5-pyrimidinyl)-2,6-dimethoxy-p-toluate.

17. A compound in accordance with claim 1, 4'-[(2,4-diamino-5-pyrimidinyl)-methyl]-2',6'-diethoxy-acetophenone.

18. A compound in accordance with claim 1, 4'-[(2,4-diamino-5-pyrimidinyl)-methyl]-2',6'-dimethoxy-acetophenone.

19. A compound in accordance with claim 1, 4-[(2,4-diamino-5-pyrimidinyl)-methyl]-2,6-dimethoxy-α-methylbenzyl alcohol.

20. A compound in accordance with claim 1, 2,4-diamino-5-[3,5-dimethoxy-4-(methoxymethyl)-benzyl]pyrimidine.

21. A compound in accordance with claim 1, 4-[(2,4-diamino-5-pyrimidinyl)-methyl]-2,6-dimethoxy-α,α-dimethylbenzyl)alcohol.

* * * * *

UNITED STATES PATENT AND TRADEMARK OFFICE
CERTIFICATE OF CORRECTION

PATENT NO. : 3,931,181
DATED : January 6, 1976
INVENTOR(S) : Ivan Kompis et al.

It is certified that error appears in the above-identified patent and that said Letters Patent are hereby corrected as shown below:

Cover Sheet after "[30] Foreign Application Priority Data

July 27, 1973    Switzerland    10995/73"

also include

June 19, 1974    Switzerland    8392/74

Column 30, claim 1, line 4, "nitrils" should be: nitrilo

Signed and Sealed this fifteenth Day of June 1976

[SEAL]

Attest:

RUTH C. MASON
*Attesting Officer*

C. MARSHALL DANN
*Commissioner of Patents and Trademarks*